United States Patent [19]

Berge et al.

[11] Patent Number: 5,077,299

[45] Date of Patent: Dec. 31, 1991

[54] IMIDAZOLE SUBSTITUTED COMPOUNDS WHICH HAVE USEFUL PHARMACEUTICAL UTILITY

[75] Inventors: John M. Berge, Epson; Lee J. Beeley, Surrey, both of England

[73] Assignee: Beecham Group p.l.c., Brentford, England

[21] Appl. No.: 493,351

[22] Filed: Mar. 14, 1990

Related U.S. Application Data

[62] Division of Ser. No. 124,902, Nov. 24, 1987, Pat. No. 4,918,083.

Foreign Application Priority Data

Nov. 27, 1986 [GB] United Kingdom ............... 8628415
Mar. 6, 1987 [GB] United Kingdom ............... 8705238

[51] Int. Cl.$^5$ .................... C07D 401/06; A61K 31/47
[52] U.S. Cl. ................................... 514/290; 514/307; 546/101; 546/148
[58] Field of Search ..................... 546/148; 514/307

[56] References Cited

U.S. PATENT DOCUMENTS 3,836,536  9/1974  Morrison et al. .................. 546/145
4,753,952  6/1988  Vecchietti et al. ................. 546/145

*Primary Examiner*—C. Warren Ivy
*Assistant Examiner*—Zinna Northington-Davis
*Attorney, Agent, or Firm*—Hopgood, Calimafde, Kalil, Blaustein & Judlowe

[57] ABSTRACT

A compound of formula (I):

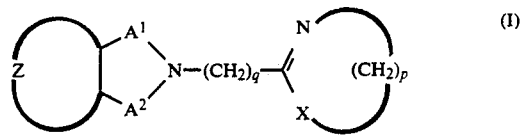

or a pharmaceutically acceptable salt, ester or amide thereof, or a pharmaceutically acceptable solvate thereof, wherein:

Z represents a residue of a substituted or unsubstituted aryl group, $A^1$ represents a substituted or unsubstituted methylene group or a substituted or unsubstituted ethylene group;

$A^2$ represents a substituted or unsubstituted methylene group or a substituted or unsubstituted ethylene group;

providing that at least one of $A^1$ or $A^2$ represents a substituted methylene group or a substituted ethylene group, X represents O or $NR^0$ wherein $R^0$ represents a hydrogen atom, a substituted or unsubstituted alkyl group, a substituted or unsubstituted aryl group, an alkanoyl group substituted or unsubstituted in the alkyl moiety, or an arylalkyl moiety substituted or unsubstituted in the aryl moiety, p represents an integer 2 or 3, and q represents an integer in the range of from 1 to 12;

a process for preparing such a compound, a composition comprising such a compound and the use of such a compound in medicine.

16 Claims, No Drawings.

IMIDAZOLE SUBSTITUTED COMPOUNDS WHICH HAVE USEFUL PHARMACEUTICAL UTILITY

This is a divisional of copending application Ser. No. 07/124,902 filed on Nov. 24, 1987, now U.S. Pat. No. 4,918,083.

This invention relates to a class of novel heterocyclic compounds having α2-adrenoceptor antagonist activity, to a process for preparing such compounds, to pharmaceutical compositions containing such compounds and the use of such compounds and compositions in medicine.

British Patent Application, Publication No. 2021100A and European Patent Specification, Publication Number 0,072,954 disclose certain heterocyclic compounds which are described as having long lasting anti-hypertensive activity.

A novel class of heterocyclic compounds has now been discovered which are structurally distinct from the GB 2021100A and EP 0,072,954 compounds. The novel heterocyclic compounds surprisingly show good α2-adrenoceptor antagonist activity and they are therefore of potential use in the treatment and/or prophylaxis of hyperglycaemia and/or glaucoma and/or the treatment of hypertension and/or depression and/or for inhibiting blood platelet aggregation.

Accordingly, the present invention provides a compound of formula (I):

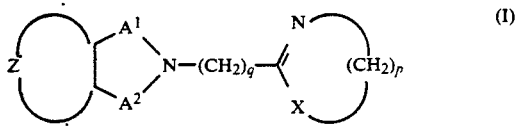

or a pharmaceutically acceptable salt, ester or amide thereof, or a pharmaceutically acceptable solvate thereof, wherein:

Z represents a residue of a substituted or unsubstituted aryl group, $A^1$ represents a substituted or unsubstituted methylene group or a substituted or unsubstituted ethylene group;

$A^2$ represents a substituted or unsubstituted methylene group or a substituted or unsubstituted ethylene group;

providing that at least one of $A^1$ or $A^2$ represents a substituted methylene group or a substituted ethylene group, X represents O or $NR^o$ wherein $R^o$ represents a hydrogen atom, a substituted or unsubstituted alkyl group, a substituted or unsubstituted aryl group, an alkanoyl group substituted or unsubstituted in the alkyl moiety, or an arylalkyl moiety substituted or unsubstituted in the aryl moiety, p represents an integer 2 or 3, and q represents an integer in the range of from 1 to 12.

Suitably Z represents the residue of a substituted or unsubstituted aryl group comprising single or fused 5- or 6- membered rings, such as a phenyl, naphthyl, anthracyl or phenanthrenyl group.

Favourably, Z represents the residue of a substituted or unsubstituted phenyl or naphthyl group.

Preferably, Z represents the residue of a substituted or unsubstituted phenyl group.

Suitably, $A^1$ or $A^2$ represent a substituted or unsubstituted methylene group.

In one preferred form of the invention, $A^1$ represents a substituted methylene group and $A^2$ represents an unsubstituted methylene group.

Suitable optional substituents for any aryl group or aryl moiety include up to 5 preferably up to 3, groups selected from halogen, alkyl, alkenyl, alkynyl, phenyl, haloalkyl, hydroxy, alkoxy, arylalkyloxy, amino, mono- and di-alkylamino, aminoalkyl, mono- and di-alkylaminoalkyl, nitro, carboxy, alkoxycarbonyl, carboxyalkyl, alkoxycarbonylalkyl, alkylcarbonyl or a moiety $SO_2NR^sR^t$ wherein $R^s$ and $R^t$ each independently represent hydrogen or alkyl, or $R^s$ and $R^t$ together with the nitrogen to which they are attached form a saturated 5- or 6- membered ring.

Suitable optional substituents for any alkyl, alkenyl or alkynyl group moiety include those mentioned above in relation to the aryl group.

It will be appreciated that the abovementioned substituents for aryl groups and aryl moieties includes substituents for those aryl groups of which Z represents a residue; aryl group substituents of $A^1$ or $A^2$ and aryl moieties forming aralkyl substituents of $A^1$ or $A^2$; aryl groups represented by $R^o$; and aryl moieties forming part of other groups represented by $R^o$.

It will be appreciated that the abovementioned substituents for alkyl, alkenyl or alkynyl groups includes alkyl, alkenyl or alkynyl substituents for $A^1$ or $A^2$; substituents for those alkyl groups represented by $R^o$ and substituents for those alkyl moieties forming part of other groups represented by $R^o$.

A preferred substituent for Z is a halogen atom, especially a fluorine or chlorine atom.

Suitable substituents for $A^1$ or $A^2$ include up to four groups selected from substituted or unsubstituted alkyl; substituted or unsubstituted alkenyl; substituted or unsubstituted alkynyl; substituted or unsubstituted aryl or aralkyl.

Favoured substituents for $A^1$ or $A^2$ include alkyl, substituted or unsubstituted phenyl or benzyl.

A preferred substituent for $A^1$ or $A^2$ is alkyl, especially $C_{1-6}$ alkyl, and in particular $C_{1-4}$ alkyl, such as methyl, ethyl or iso- propyl.

A preferred substituent for $A^1$ or $A^2$ is a phenyl group or a substituted phenyl group, suitably substituted with a halogen atom, especially a fluorine or a chlorine atom, an alkyl group, especially a $C_{1-6}$ alkyl group and in particular a $C_{1-4}$ alkyl group such as a methyl group, an alkoxy group, especially a $C_{1-6}$ alkoxy group and in particular a $C_{1-4}$ alkoxy group, such as a methoxy group.

A preferred substituent for $A^1$ or $A^2$ is a benzyl group.

Suitably, X represents $NR^o$.

Suitably, $R^o$ represents hydrogen, alkyl or alkanoyl.

Preferably, $R^o$ represents hydrogen.

Suitably, q represents an integer in the range of from 1 to 6.

In one aspect the present invention provides a compound, falling wholly within the scope of formula (I), of formula (II):

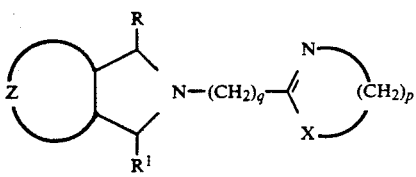

or a pharmaceutically acceptable salt, ester or amide thereof, or a pharmaceutically acceptable solvate thereof, wherein:

Z, X, p and q are as defined in relation to formula (I), R and $R^1$ each independently represents hydrogen, substituted or unsubstituted alkyl, substituted or unsubstituted alkenyl, substituted or unsubstituted alkynyl, substituted or unsubstituted aryl or aralkyl substituted or unsubstituted in the aryl moiety; providing that only one of R and $R^1$ represents hydrogen.

Suitably, R and $R^1$ each independently represents hydrogen, alkyl, substituted or unsubstituted aryl or aralkyl providing that only one of R and $R^1$ represents hydrogen.

Suitably, R and $R^1$ each independently represents hydrogen, alkyl or substituted or unsubstituted aryl, providing that only one of R and $R^1$ represents hydrogen.

Favourably, R and $R^1$ each independently represent hydrogen, alkyl, substituted or unsubstituted phenyl or a benzyl group providing that only one of R and $R^1$ represents hydrogen.

Preferably $R^1$ represents hydrogen.

When R or $R^1$ represents an alkyl group it is preferably an unsubstituted alkyl group, in particular an unsubstituted $C_{1-6}$ alkyl group, such as methyl, ethyl or propyl.

A preferred aryl group represented by R or $R^1$ is a substituted or unsubstituted phenyl group.

A preferred aralkyl group represented by R or $R^1$ is a benzyl group.

Favourably, R represents alkyl, especially $C_{1-6}$ alkyl, and in particular $C_{1-4}$ alkyl, such as methyl, ethyl, or propyl and $R^1$ represents hydrogen. An example of a propyl group is an iso-propyl group.

Favourably, R represents a phenyl group or a substituted phenyl group and $R^1$ represents hydrogen.

Favourably, R represents a benzyl group and $R^1$ represents hydrogen.

Thus, in particular R represents alkyl, substituted or unsubstituted phenyl or a benzyl group and $R^1$ represents hydrogen.

Suitable substituents for R and $R^1$ include halogen, hydroxy, alkyl, alkoxy, carboxy, alkoxycarbonyl, aminocarbonyl, mono- and di-alkylaminocarbonyl or a group $SO_2NHR^s$ wherein $R^s$ represents alkyl.

Preferably, R or $R^1$ independently represents hydrogen; $C_{1-6}$ alkyl, especially methyl, ethyl or propyl; phenyl; halophenyl, especially chlorophenyl or fluorophenyl; alkylphenyl, especially $C_{1-6}$ alkylphenyl such as methylphenyl; alkoxyphenyl, especially $C_{1-6}$ alkoxyphenyl such as methoxyphenyl or benzyl; providing that only one of $R^1$ and $R^2$ represents hydrogen.

Thus in particular R represents $C_{1-6}$ alkyl, especially methyl, ethyl or propyl; phenyl; halophenyl, especially chlorophenyl or fluorophenyl; alkylphenyl, especially $C_{1-6}$ alkylphenyl such as methylphenyl; alkoxyphenyl, especially $C_{1-6}$ alkoxyphenyl such as methoxyphenyl or benzyl and $R^1$ represents hydrogen.

Most preferably R or $R^1$ independently represent hydrogen; methyl; ethyl; propyl; phenyl; monochlorophenyl, especially 3- or 4-chlorophenyl; monofluorophenyl, especially 4-fluorophenyl; monoalkylphenyl, especially mono-$C_{1-6}$-alkylphenyl such as 4-methylphenyl; monoalkoxyphenyl, especially mono $C_{1-6}$-alkoxyphenyl, such as 4-methoxyphenyl or benzyl.

Thus in particular R represents hydrogen; methyl; ethyl; propyl; phenyl; monochlorophenyl, especially 3- or 4-chlorophenyl; monofluorophenyl, especially 4-fluorophenyl; monoalkylphenyl, especially mono-$C_{1-6}$ alkylphenyl such as 4-methylphenyl; monoalkoxyphenyl, especially mono-$C_{1-6}$-alkoxyphenyl, such as 4-methoxyphenyl or benzyl and $R^1$ represents hydrogen.

In an especially favoured aspect, R represents methyl, ethyl, or isopropyl, especially methyl or ethyl, and $R^1$ represents hydrogen.

In an especially preferred aspect R represents phenyl, 4-fluorophenyl, 3-chlorophenyl, 4-chlorophenyl, 4-methylphenyl, 4-methoxyphenyl or benzyl and $R^1$ represents hydrogen.

In the most preferred aspect R represents methyl or ethyl and $R^1$ represents hydrogen.

Preferably X represents NH.

Preferably, p represents the integer 2.

Preferably, q represents the integer 1.

The present invention particularly provides a group of compounds, falling within the scope of formula (I), of formula (III);

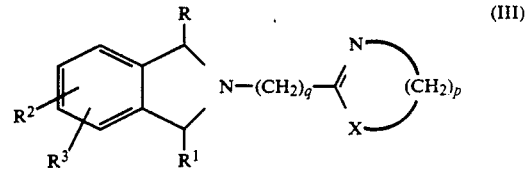

or a pharmaceutically acceptable salt, ester or amide thereof, or a pharmaceutically acceptable solvate thereof, wherein R, $R^1$, X, p and q are as defined above and $R^2$ and $R^3$ each independently represents hydrogen, alkyl, amino, mono- or di-alkyl amino, hydroxy, alkoxy, carboxy, or a halogen atom.

Suitably, $R^2$ or $R^3$ independently represent hydrogen or halogen.

Suitably, $R^2$ represents halogen, especially fluorine or chlorine.

Suitably, $R^3$ represents hydrogen.

Preferably, $R^2$ represents halogen, especially fluorine or chlorine and $R^3$ represents hydrogen.

In a further preferred aspect $R^2$ and $R^3$ both represent hydrogen.

Certain of the compounds of the present invention may exist in one or more stereoisomeric forms. The present invention encompasses all such isomeric forms whether free from other isomers or admixed with any other isomer in any proportion, and thus includes racemic mixtures of enantiomers.

Suitable pharmaceutically acceptable salts of the compound of formula (I) include acid addition salts, salts of carboxy groups and salts of hydroxy groups, especially acid addition salts.

Suitable pharmaceutically acceptable acid addition salts of compound (I) include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphonate, α-keto glutarate, α-glycerophosphate, and glucose-1-phosphate. Preferably the acid addition salt is a hemisuccinate, hydrochloride, α-ketoglutarate, α-glycerophosphate or glucose-1-phosphate, in particular the hydrochloride salt, including the dihydrochloride.

Suitable pharmaceutically acceptable salts of carboxy groups include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl) -amine, cycloalkylamines such as bicyclohexylamine, or with procaine, 2 dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable salts of hydroxyl groups include metal salts, especially alkali metal salts such as sodium and potassium salts.

Suitable pharmaceutically acceptable esters of compounds of formula (I) include esters of carboxy groups and hydroxy groups.

Favoured pharmaceutically acceptable esters are in-vivo hydrolysable esters of carboxy groups and hydroxy groups.

Examples of suitable in-vivo hydrolysable esters of carboxyl groups include those which break down readily in the human body to leave the parent acid or its salt. Suitable ester groups of this type include those of part formula (i), (ii) and (iii):

$$-CO_2CH\text{-}O.CO.R^b \quad \overset{R^a}{|} \quad \text{(i)}$$

$$-CO_2R^c\text{-}N\overset{R^d}{\underset{R^e}{|}} \quad \text{(ii)}$$

$$-CO_2CH_2OR^f \quad \text{(iii)}$$

wherein $R^a$ is hydrogen, methyl, or phenyl, $R^b$ is $C_{1-6}$ alkyl, $C_{1-6}$ alkoxy or phenyl; or $R^a$ and $R^b$ together form a 1,2-phenylene group optionally substituted by one or two methoxy groups;

$R^c$ represents $C_{1-6}$ alkylene optionally substituted with a methyl or ethyl group -

$R^d$ and $R^e$ independently represent $C_{1-6}$ alkyl;

$R^f$ represents $C_{1-6}$ alkyl.

Examples of suitable in vivo hydrolysable ester groups include for example acyloxyalkyl groups such as acetoxymethyl, pivaloyloxy-methyl, α-acetoxyethyl and α-pivaloyloxyethyl groups; alkoxycarbonyloxyalkyl groups, such as ethoxycarbonyl-oxymethyl and α-ethoxycarbonyloxyethyl; dialkylamino-alkyl especially di-loweralkylamino alkyl groups such as dimethylaminomethyl, dimethylaminoethyl, diethylaminomethyl or diethylaminoethyl and lactone groups such as phthalidyl and dimethoxyphthalidyl.

Suitable in-vivo hydrolysable esters of hydroxyl groups include those provided by $C_{1-6}$ alkyl carboxylic acids.

Suitable pharmaceutically acceptable amides include amides of formula —CO. $NR^sR^t$ wherein $R^s$ and $R^t$ each independently represent hydrogen or $C_{1-6}$ alkyl; or $R^s$ and $R^t$ together with the nitrogen to which they are attached represent a saturated 5- or 6- membered ring.

Suitable pharmaceutically acceptable solvates includes hydrates.

When used herein the term "halogen" refers to fluorine, chlorine, bromine and iodine; preferably chlorine.

When used herein the term "in-vivo" hydrolysable ester" relates to a pharmaceutically acceptable ester which readily breaks down in the human or non-human animal body to leave for example in relation to an in-vivo hydrolysable ester of a carboxy group the free carboxy group or a salt thereof or for example in relation to an in-vivo hydrolysable ester of an hydroxy group, the free hydroxy group, or a salt thereof.

When used herein the term "alkyl", "alkenyl", "alkynyl" or "alkoxy" relates to groups having straight or branched chains containing up to 12 carbon atoms.

Suitable alkyl groups are $C_{1-12}$ alkyl groups especially $C_{1-6}$ alkyl groups e.g. methyl, ethyl, n-propyl, iso-propyl, n-butyl, isobutyl or tert-butyl groups.

Suitable alkenyl groups are $C_{2-12}$ groups especially $C_{2-6}$ alkenyl groups.

Suitable alkynyl groups are $C_{2-12}$ alkynyl groups especially $C_{2-6}$ alkynyl groups.

The present invention also provides a process for the preparation of a compound of formula (I), or a pharmaceutically acceptable salt, ester or amide thereof, or a pharmaceutically acceptable solvate thereof, which process comprises cyclising a compound of formula (IV):

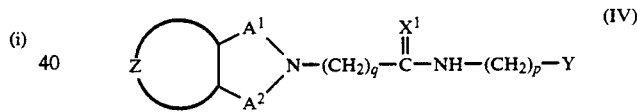

wherein Z, $A^1$, $A^2$, p and q are as defined in relation to formula (I), $X^1$ represents O or NH and Y represents $OR^g$ wherein $R^g$ is hydrogen or a hydroxyl protecting group, or —$NHR^h$ wherein $R^h$ represents hydrogen or a nitrogen protecting group; providing that when $X^1$ is O then Y is $OR^g$ and when $X^1$ is NH then Y is $NHR^h$;

and thereafter if required carrying out one or more of the following optional steps:

(i) removing any protecting groups;

(ii) converting a compound of formula (I) into a further compound of formula (I);

(iii) converting a compound of formula (I) into a pharmaceutically acceptable salt, ester or amide thereof, or a pharmaceutically acceptable solvate thereof;

Preferably, $R^h$ represents hydrogen.

A compound of formula (IV) may be prepared by reacting a compound of formula (V):

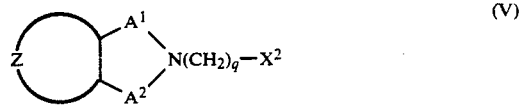

wherein Z, $A^1$, $A^2$ and q are as defined in relation to formula (I) and $X^2$ represents CN, or $CO_2R^4$ wherein $R^4$ represents hydrogen or an alkyl group, with a compound of formula (VI):

$$H_2N-(CH_2)_p-Y \qquad (VI)$$

wherein p is defined in relation to formula (I) and Y represents $OR^g$ when $X^2$ is $-CO_2R^4$ and Y represents $-NR^h$ when $X^2$ is CN.

Preferably, Y represents $-NR^h$, as defined above, and $X^2$ represents CN.

A compound of formula (V) may be prepared by reacting a compound of formula (VII):

wherein Z, $A^1$ and $A^2$ are as defined in relation to formula (I) and $R^x$ represents a leaving group, with a compound of formula (VIII):

$$H_2N-(CH_2)_q-X^2 \qquad (VIII)$$

or an acid addition salt thereof, preferably a hydrochloride, wherein q and $X^2$ are as defined in relation to formula (V).

Suitably, $R^x$ represents a halogen atom, preferably a chlorine or bromine atom, especially a bromine atom.

The compounds of formulae (VI) and (VIII) are either known commercially available compounds or may be prepared using methods analogous to those used to prepare such compounds.

The compounds of formula (VII) are either known compounds or may be prepared using methods analogous to those used to prepare known compounds: for example by using the methods disclosed in Helv. Chim. Acta, 1977, 60, 2872, J. Chem. Soc., Perkin I, 1972, 2732 and Bull. Soc. Chim. France, 1953, 321.

The cyclisation of compounds of formula (IV) may be carried out under any appropriate conditions, using any suitable solvent system and temperature range, but usually at an elevated temperature.

Favourably for compounds of formula (I) wherein X represents O, the cyclisation of the compound of formula (IV) is carried out in the presence of a dehydrating agent, such as phosphoryl chloride. Conveniently the reaction is carried out in toluene, or any other suitable solvent, preferably at the reflux temperature of the chosen solvent.

Suitably, for the preparation of compounds of formula (I) wherein X represents $NR^o$, the compounds of formula (IV) from the reaction between the appropriate compounds of formula (V) and (VI) are not isolated but are converted in-situ to compounds of formula (I).

Favourably, for the preparation of compounds of formula (I) wherein X represents $-NR^o$; the appropriate compounds of formula (V) and formula (VI) are reacted together at an elevated temperature, for example within the range 80° C. to 130° C., preferably 110° C., in any suitable solvent; the reaction is preferably carried out using the appropriate compound of formula (VI) as solvent in the presence of a catalytic amount of carbon disulphide; preferably the reaction is carried out under an atmosphere of nitrogen. It will be understood that under the abovementioned conditions the compound of formula (IV) initially formed undergoes cyclisation to give the compound of formula (I).

Thus in an alternative aspect the present invention provides a process for the preparation of a compound of formula (I) wherein X represents $NR^o$, which process comprises reacting a compound of the hereinbefore defined formula (V) providing that $X^2$ represents CN, with a compound of the hereinbefore defined formula (VI) providing that Y represents $NR^o$; and thereafter if required carrying out one or more of the following optional steps:
(i) removing any protecting groups;
(ii) converting a compound of formula (I) into a further compound of formula (I);
(iii) converting a compound of formula (I) into a pharmaceutically acceptable salt, ester or amide thereof, or a pharmaceutically acceptable solvate thereof.

The reaction between compounds of formula (VII) and (VIII) is conveniently carried out in an aprotic solvent, such as dimethylformamide, preferably at a temperature of between 20° C. and 60° C.; the reaction being continued until conventional monitoring techniques indicate that the reaction is suitably complete.

Suitable hydroxyl and nitrogen protecting groups are those used conventionally in the art; for example a suitable hydroxyl protecting group is a benzyl group.

A preferred nitrogen protecting group $R^h$ is a moiety $R^o$, as defined in relation to formula (I), but not including hydrogen.

A compound of formula (I) may be converted into a further compound of formula (I) by using any appropriate conventional method, for example compounds wherein $R^o$ is hydrogen may be converted into a compound wherein $R^o$ is other than hydrogen by conventional alkylation, arylation, alkanoylation or aralkylation methods. Similarly compounds of formula (I) wherein $R^o$ is other than hydrogen may be converted to compounds of formula (I) wherein $R^o$ is hydrogen by conventional dealkylation, dearylation, dealkanoylation or dearylalkylation methods.

Salts, esters, amides and solvates of the compounds of formula (I) may be prepared using any appropriate conventional procedure compatible with the nature of the salt, ester, amide or solvate and the compound of formula (I).

Any individual isomer of a compound of formula (I), or a pharmaceutically acceptable salt, ester or amide thereof, or a pharmaceutically acceptable solvate thereof, may be prepared using any suitable known method. For example, any mixture of enantiomers may be separated into individual stereoisomers by using an optically active acid as a resolving agent. Suitable optically active acids which may be used as resolving agents are described in "Topics in Stereochemistry", Volume 6, Wiley Interscience, 1971, Allinger, N. L. and Eliel, W. L. Eds. When appropriate, the compounds of formula (I) may be separated into diastereoisomeric pairs of enantiomers by, for example, fractional crystallization from a suitable solvent such as methanol, ethyl acetate or a mixture thereof.

Alternatively, any required enantiomer of a compound of formula (I), or a pharmaceutically acceptable salt, ester or amide thereof, or a pharmaceutically acceptable solvate thereof, may be obtained by conventional stereospecific synthesis using optically pure starting materials of known configuration.

The absolute stereochemistry of any compound of formula (I), or substrate thereof, may be determined by conventional procedures, such as X-ray crystallography.

The present invention also provides a compound of formula (I), or a pharmaceutically acceptable salt, ester or amide thereof, or a pharmaceutically acceptable solvate thereof, for use as an active therapeutic substance.

The present invention provides a compound of formula (I), or a pharmaceutically acceptable salt, ester or amide thereof, or a pharmaceutically acceptable solvate thereof, for use in the treatment of and/or prophylaxis of hyperglycaemia.

In a further aspect the present invention also provides a compound of formula (I) or a pharmaceutically acceptable salt, ester or amide thereof, or a pharmaceutically acceptable solvate thereof, for use in the treatment and/or prophylaxis of glaucoma and/or the treatment of depression and/or for inhibiting blood platelet aggregation.

In a further aspect, the present invention provides a compound of formula (I), or a pharmaceutically acceptable salt, ester or amide thereof, or a pharmaceutically acceptable solvate thereof, for use in the treatment of hypertension.

A compound of the (I), or a pharmaceutically acceptable salt, ester or amide thereof, or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a pharmaceutically acceptable salt, ester or amide thereof, or a pharmaceutically acceptable solvate thereof, and a pharmaceutically acceptable carrier therefor.

As used herein the term "pharmaceutically acceptable" embraces compounds, compositions and ingredients for both human and veterinary use: for example the term "pharmaceutically acceptable salt" embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection, percutaneous absorption, and, especially for the treatment and/or prophylaxis of glaucoma, topical application to the eye, are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate, sodium lauryl sulphate or sucrose. Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

As indicated above in relation to the treatment and/or prophylaxis of glaucoma, a compound of formula (I), or a pharmaceutically acceptable salt, ester or amide thereof, or a pharmaceutically acceptable solvate thereof, may also be administered as a topical formulation in combination with conventional topical excipients. Such formulations will of course be suitably adapted for administration to the eye.

The topical formulations of the present invention may be presented as, for instance, eye ointments, creams or lotions or eye drops or other conventional formulations suitable for administration to the eye, and may contain appropriate conventional additives such as preservatives, solvents to assist drug penetration and emollients in ointments and creams. The formulations may also contain compatible conventional carriers, such as eye ointment, cream or lotion and solvents suitable for administration to the eye. Such carriers may be present as from about 20% up to about 99.5 of the formulation.

Suitable eye ointments, creams or lotions, eye drops or other conventional formulations suitable for administration to the eye are conventional formulations well known in the art, for example, as described in standard text books of pharmaceutics and cosmetics, such as Harry's Cosmeticology published by Leonard Hill Books, Remington's Pharmaceutical Sciences, and the British and US Pharmacopoeias.

Suitably, the compound of formula (I) or a pharmaceutically acceptable salt, ester or amide thereof, or a pharmaceutically acceptable solvate thereof, will comprise from about 0.5 to 20% by weight of the formulation, favourably from about 1 to 10% for example 2 to 5%.

The present invention further provides a method for the treatment and/or prophylaxis of hyperglycaemia in a human or non-human mammal which comprises administering an effective, non-toxic, amount of a compound of the general formula (I), or a pharmaceutically acceptable salt, ester or amide thereof, or a pharmaceutically acceptable solvate thereof, to a human or non-human mammal in need thereof.

The present invention further provides a method for the treatment of hypertension in a human or non-human mammal, which comprises administering an effective, non-toxic, amount of a compound of the general formula (I), or a pharmaceutically acceptable salt, ester or amide thereof, or a pharmaceutically acceptable solvate thereof, to a human or non-human mammal in need thereof.

The invention also provides a method for the treatment and/or prophylaxis of glaucoma and/or the treatment of depression and/or inhibiting blood platelet aggregation in a human or non-human mammal, which method comprises administering an effective non-toxic amount of a compound of formula (I), or a pharmaceutically acceptable salt, ester or amide thereof, or a pharmaceutically acceptable solvate thereof, to a human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans or the treatment of hypertensive humans the compound of formula (I), or a pharmaceutically acceptable salt, ester or amide thereof, or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be administered by mouth, usually once or twice a day and in an amount in the range of from about 0.025 mg/kg to 25 mg/kg, for example 0.1 mg/kg to 20 mg/kg.

In the treatment and/or prophylaxis of glaucoma (via non-topical regimes) and the treatment of depression and inhibition of platelet aggregation in human or non-human mammals, dosage regimes are as indicated above for the treatment and/or prophylaxis of hyperglycaemic human or non-human mammals.

The present invention also provides the use of a compound of formula (I), or a pharmaceutically acceptable salt, ester or amide thereof, or a pharmaceutically acceptable solvate thereof, for the manufacture of a medicament for the treatment and/or prophylaxis of hyperglycaemia and/or the treatment of hypertension.

The present invention further provides the use of a compound of formula (I) or a pharmaceutically acceptable salt, ester or amide thereof, or a pharmaceutically acceptable solvate thereof, for the manufacture of a medicament for the treatment and/or prophylaxis of glaucoma and/or the treatment of depression and/or for the inhibition of blood platelet aggregation.

No toxicological effects are indicated when a compound of formula (I), or a pharmaceutically acceptable salt, ester or amide thereof, or a pharmaceutically acceptable solvate thereof, is administered in any of the abovementioned dosage ranges.

The following Examples illustrate the invention but do not limit it in any way.

A summary of the examples of the invention are shown below:

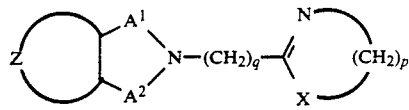

| Ex. No. | Z | $A^1$ | $A^2$ | X | p | q |
|---|---|---|---|---|---|---|
| 1 | 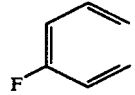 | CH$_3$CH | CH$_2$ | NH | 2 | 1 |
| 2 |  | EtCH | CH$_2$ | NH | 2 | 1 |
| 3 |  | CH$_3$CH | CH$_2$ | NH | 2 | 1 |
| 4 |  | CH$_3$CH | CH$_2$ | NH | 2 | 1 |

-continued

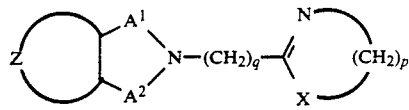

| Ex. No. | Z | $A^1$ | $A^2$ | X | p | q |
|---|---|---|---|---|---|---|
| 5 |  | CH$_3$CH | CH$_2$ | NH | 2 | 1 |
| 6 |  | 4-ClC$_6$H$_4$—CH | CH$_2$ | NH | 2 | 1 |
| 7 |  | 3-ClC$_6$H$_4$—CH | CH$_2$ | NH | 2 | 1 |
| 8 |  | 4-FC$_6$H$_4$—CH | CH$_2$ | NH | 2 | 1 |
| 9 |  | PhCH | CH$_2$ | NH | 2 | 1 |
| 10 |  | iPrCH | CH$_2$ | NH | 2 | 1 |
| 11 |  | 4-CH$_3$C$_6$H$_4$—CH | CH$_2$ | NH | 2 | 1 |
| 12 |  | 4-CH$_3$OC$_6$H$_4$—CH | CH$_2$ | NH | 2 | 1 |
| 13 |  | PhCH$_2$—CH | CH$_2$ | NH | 2 | 1 |

EXAMPLE 1

2-[2H-(1-Methyl-1,3-dihydroisoindole)methyl]-4,5-dihydroimidazole

A mixture of 3.44 g (20 mM) of 2H-(b-methyl 1,3-dihydroisoindole)-2-acetonitrile, 1.22 g (20 mM) of 1,2-diaminoethane and a catalytic amount of carbon disulphide was heated at 110° C. under nitrogen for 6 hours. The mixture was allowed to cool and solidify; 50 ml of water was added to the resultant crystalline mass and filtration gave a yellow solid. Recrystallisation from ethyl acetate afforded the title compound as a white solid, m.p. 121–125° C. (decomp.).

$^1$H-nmr δ (CDCl$_3$).

7.3–7.1 (4H, m), 5.2–4.8 (1H, broad m, exchanges with D$_2$O), 4.21 (1H, dd), 3.91 (1H, q), 3.8–3.5 (6H, m); 3.40 (1H, d); 1.41 (3H, d).

IR (KBr): 1612 cm$^{-1}$

EXAMPLE 2

2-[2H-(1-Ethyl-1,3-dihydroisoindole)methyl]-4,5-dihydroimidazole dihydrochloride This compound was prepared in an analogous manner to Example 1 from 3.72 g (20 mM) of 2H-(1-ethyl-1,3-dihydroisoindole)-2-acetonitrile and 1.22 g (20 mM) of 1,2-diaminoethane. The resultant crude product was dissolved in ethanol and treated with dry hydrogen chloride. The title compound crystallised from solution on cooling, m.p. 182–184° C.

$^1$H-nmr δ (DMSO)

11.0–10.5 (3H, broad s, exchanges with D$_2$O); 7.5–7.2 (4H,m); 4.7–4.6 (1H,m); 4.4–4.1 (2H,m); 4.0–3.7 (6H,m); 2.2–1.7 (2H,m); 0.94 (3H,t).

EXAMPLE 3

2-[2H-(5-Chloro-1-methyl-1,3-dihydroisoindole)methyl]4,5-dihydroimidazole dihydrochloride This compound was prepared in an analogous manner to Example 1 from 3.50 g (20 mM) of 2H-(5-chloro-1-methyl-1,3-dihydroisoindole)-2-acetonitrile and 1.22 g (20 mmol) of 1,2-diaminoethane to give the title compound, m.p. 152–3° C. (isopropanol/ethyl acetate).

$^1$H-nmr δ (DMSO)

10.7–10.4 (3H,broad s, exchanges with D$_2$O); 7.5–7.2 (3H,m); 4.5–4.0 (5H, m); 3.88 (4H,s); 1.52 (3H, d).

EXAMPLE 4

2-[2H-(6-Chloro-1-methyl-1,3-dihydroisoindole)methyl]-4,5-dihydroimidazole.

This compound was prepared in an analogous manner to Example 1 from 2.50 g (12 mM) of 2H-(6-chloro-1-methyl-1,3-dihydroisoindole)-2-acetonitrile and 1.1 g (18 mM) of 1,2-diaminoethane to yield the title compound, m.p. 158–160° C. (ethyl acetate).

$^1$H-nmr δ (CDCl$_3$)

7.3–7.0 (3H, m); 5.0–4.5 (1H, broad s exchanges with D$_2$O); 4.24 (1H,d); 3.95 (1H,q); 3.7–3.5 (6H, m); 3.41 (1H,d); 1.39 (3H,d).

EXAMPLE 5

2[2H-(5-Fluoro-1-methyl-1,3-dihydroisoindole)methyl]-4,5-dihydroimidazole

This compound was prepared in an analogous manner to Example 1 from 2.11 g (11 mM) of 2H-(5-fluoro-1-methyl-1,3-dihydroisoindole)-2-acetonitrile and 1.1 g (18 mM) of 1,2-diaminoethane to yield the title compound, m.p. 120–122° C. (ethyl acetate).

$^1$H-nmr δ (CDCl$_3$)

7.3–7.0 (1H,m); 6.9–6.8 (2H,m); 5.0–4.5 (1H broad s exchanges with D$_2$O); 4.17 (1H,d); 3.78 (1H,q); 3.7–3.5 (6H,m); 3.40 (1H,d); 1.39 (3H,d).

EXAMPLE 6

2-[2H-(1-(4-Chlorophenyl)-1,3-dihydroisoindole)methyl]-4,5-dihydroimidazole

The title compound, m.p. 167–9° C. (ethyl acetate) was prepared from 10.5 g (38 mM) of 2H-(1-(4-chlorophenyl)-1,3-dihydroisoindole)-2-acetonitrile and 2.43 g (40 mM) of 1,2-diaminoethane by an analogous procedure to that described in Example 1.

$^1$H-nmr δ (DMSO)

6.67–7.6 (8H,m); 5.0 (1H,brs); 4.4 (1H,dd); 3.9 (1H,dd) and 3.35 (6H, brs).

EXAMPLE 7

2-[2H-1-(3-Chlorophenyl)-1,3-dihydroisoindole)methyl]4,5-dihydroimidazole)

The title compound, m.p. 159–160° C. (ethyl acetate) was prepared from 14.7 g (54 mM) of 2H-1[1-(3-chlorophenyl)-1,3-dihydroisoindole]-2-acetonitrile and 3.4 g (57 mM) of 1,2-diaminoethane by an analogous procedure to that described in Example 1.

$^1$H nmr δ (CDCl$_3$)

6.65–7.45 (8H, m); 4.8 (1H, brs); 4.55 (1H, brs, exchanges with D$_2$O); 4.4 (1H, dd); 3.85 (1H, dd); 3.48 (2H, s) and 3.4 (4H, brs).

EXAMPLE 8

2-[2H-(1-(4-Fluorophenyl)-1,3-dihydroisoindole)methyl]-4,5-dihydroimidazole

The title compound, m.p. 168–169° C. (ethyl acetate) was prepared from 7.0 g (27 mM) of 2H-(1-(4-fluorophenyl)-1,3-dihydroisoindole)-2-acetonitrile and 1.8 g (30 mM) of 1,2-diaminoethane by an analogous procedure to that described in Example 1.

$^1$H nmr δ (DMSO)

6.65–7.55 (8H, m); 4.8 (1H, brs); 4.5 (1H, brs, exchanges with D$_2$O); 4.4 (1H, dd); 3.9 (1H, dd); 3.45 (2H, s) and 3.35 (4H, brs).

EXAMPLE 9

2-[2H-(1-Phenyl-1,3-dihydroisoindole)methyl]-4,5-dihydroimidazole

The title compound, m.p. 168–170° C. (ethyl acetate), was prepared from 3.5 g (15 mM) of 2H-(1-phenyl-1,3-dihydroisoindole)-2-acetonitrile and 0.9 g (15 mM) of 1,2-diaminoethane by an analogous procedure to that described in Example 1.

$^1$H nmr δ (CDCl$_3$)

7.4–6.6 (9H, m); 4.75 (1H, brs); 4.35 (1H, dd); 3.82 (1H, dd); 3.5 (2H, s) and 3.4 (4H, brs).

EXAMPLE 10

2-(2H-[1-(1-Methylethyl)-1,3-dihydroisoindole]methyl)-4,5-dihydroimidazole dihydrochloride hemihydrate.

This compound was prepared in an analogous manner to Example 1 from 1.0 g (5 mM) of 2H-[1-(1-methylethyl)-1,3-dihydroisoindole]-2-acetonitrile and 0.4ml (7.4 mM) of 1,2-diaminoethane to yield the crude compound. Chromatography over neutral alumina eluting with dichloromethane/methanol (0 3%) yielded an oil. This oil was dissolved in ethanol and converted to the dihydrochloride with hydrogen chloride. The ethanol was evaporated and residue crystallised from ethanol/ethyl acetate to yield the title compound, m.p. 188–190° C.

$^1$H-nmr δ (DMSO)

10.2–10.0 (2H,broad signal, exchanges with D$_2$O); 7.27 (4H,s); 4.7–4.3 (1H, broad signal, exchanges with D$_2$O); 4.47 (1H,d); 4.17 (1H,s); 4.00 (1H,d); 3.6–3.4 (6H,m); 2.2–2.20 (1H,m); 0.93 (3H,d); 0,89 (3H,d).

EXAMPLE 11

2-[2H-(1-(4-Methylphenyl)-1,3-dihydroisoindole)methyl]-4,5-dihydroimidazole.

The title compound, m.p. 158–160° C. (ethyl acetate), was prepared from 10.3 g (41mM) of 2H-(1-(4-methylphenyl)-1,3-dihydroisoindole)-2-acetonitrile and 2.7 g (45 mM) of 1,2-diaminoethane by an analogous procedure to that described in Example 1.

$^1$H-nmr δ (DMSO+CDCl$_3$)
6.6–7.45 (8H,m); 4.8 (1H,brs); 4.35 (1H,dd); 3.82 (1H,dd); 3.38 (6H,brs) and 2.3 (3H,s).

EXAMPLE 12

2-[2H-(1-(4-Methoxyphenyl)-1,3-dihydroisoindole)methyl]-4,5-dihydroimidazole.

The title compound, m.p. 162–163° C. (ethyl acetate), was prepared from 10.4 g (39 mM) of 2H-(1-methoxyphenyl)-1,3-dihydroisoindole)-2-acetonitrile and 2.6 g (43 mM) of 1,2-diaminoethane by an analogous procedure to that described in Example 1.

$^1$H-nmr δ (CDCl$_3$)
6.65–7.4 (8H, m); 4.75 (1H, s); 4.4 (1H, dd); 3.85 (1H, dd); 3.8 (3H, s); 3.5 (2H, brs) and 3.4 (4H, brs).

EXAMPLE 13

2-[2H-(1-Benzyl-1,3-dihydroisoindole)methyl]-4,5-dihydroimidazole.

The title compound, m.p. 132–134° C. (ethyl acetate), was prepared from 4 g (16 mM) of 2H-(1-benzyl-1,3-dihydroisoindole)-2-acetonitrile and 1.1 g (18 mM) of 1,2-diaminoethane by an analogous procedure to that described in Example 1.

$^1$H nmr δ (CDCl$_3$)
7.35–7.0 (9H, m), 4.25 (2H, m); 3.75 (1H, d), 3.55 (4H, brs); 3.4 (2H, q) and 3.05 (2H, d).

EXAMPLE X1

1-(1-hydroxyethyl)-2-hydroxymethylbenzene

To a suspension of 12 g of lithium aluminium hydride in 50 ml of dry diethyl ether was added dropwise with stirring a solution of 25 g (152.4 mM) of 2-acetylbenzoic acid in 120 ml of dry tetrahydrofuran. After heating under reflux for 6 hours, the mixture was cooled and treated carefully with 12 ml of water, 12 ml of 10% sodium hydroxide solution and 24 ml of water. The solution was filtered, the filtrate was dried over magnesium sulphate, filtered and evaporated to yield the title compound as a colourless waxy solid.

$^1$H nmr δ (CDCl$_3$)
7.4–7.0 (4H,m); 4.9(1H,q); 4.48(1H, broad s); 3.98(2H, broad s, exchanges with D$_2$O); 1.4(3H,d).

EXAMPLE X2

1-(1-Bromoethyl)-2-bromomethyl benzene

To a solution of 22 g (144.7 mM) of 1-(1-hydroxyethyl)-2-hydroxymethylbenzene in 150 ml of dry diethyl ether was added dropwise with stirring 58 ml (611 mM) of phosphorous tribromide in 250 ml of diethyl ether while the temperature of the reaction was kept below 30° C. After stirring at room temperature for 18 hours the resultant solution was poured into ice/water (500 ml). The aqueous layer was saturated with sodium chloride and the organic layer separated, dried and evaporated to yield the title compound bp. 115–117° C./0.5 mm.

$^1$H-nmr δ (CDCl$_3$).
7.8–7.4 (1H, m); 7.4–7.2 (3H, m); 5.60 (1H, q); 4.78 (1H, d); 4.39 (1H, d); 2.05 (3H, d).

EXAMPLE X3

2H-(1-Methyl-1,3-dihydroisoindole)-2-acetonitrile

To a mixture of 10 g (108 mM) of aminoacetonitrile hydrochloride and 40 ml (294 mM) of triethylamine in 200 ml of dry dimethylformamide at 50° C. under nitrogen was added dropwise with stirring 27 g (97 mM) 1-(1-bromoethyl-2-bromomethylbenzene in 100 ml of dry dimethylformamide. The reaction temperature was kept below 60° C. during the addition. After stirring overnight at room temperature the mixture was poured into 600 ml of water, the organic product was extracted with 3×500 ml portions of diethyl ether. The organic layer was washed with water (×1) and saturated sodium chloride solution (×1), dried and evaporated to yield the crude nitrile. Vacuum distillation afforded the title compound as a pale yellow oil, b.p. 108–112° C./0.4 mm.

$^1$H-nmr δ (CDCl$_3$).
7.4–7.0 (4H, m); 4.3–3.7 (3H, m); 3.75 (2H, s); 1.39 (3H, d).

EXAMPLE X 4

1-(1-Hydroxypropyl)-2-hydroxymethylbenzene

This compound was prepared in an analogous manner to Example XI from 10 g (56 mM) of propiophenone-2-carboxylic acid and lithium aluminium hydride to yield the title compound as an oil.

$^1$H-nmr δ (CDCl$_3$)
7.5–7.2 (4H, m); 4.8–4.5 (3H,m); 3.9–3.5 (2H, broad s, exchanges with D$_2$O); 1.9–1.6 (2H, m); 0.86 (3H,t).

EXAMPLE X 5

1-(1-bromopropyl)-2-bromomethylbenzene

This compound was prepared in an analogous manner to Example X2 from 7.3 g (44 mM) of 1-(1-hydroxypropyl)-2-hydroxymethylbenzene and phosphorus tribromide to yield the title compound as a pale yellow oil.

$^1$H-nmr δ (CDCl$_3$)
7.5–7.1 (4H,m); 5.31 (1H,t); 4.71 (1H,d); 4.41 (1H, d); 2.6–2.1 (2H,m); 1.09 (3H,t).

EXAMPLE X 6

2H-(1-Ethyl-1,3-dihydroisoindole)-2-acetonitrile

This compound was prepared in an analogous manner to Example X3 from 13 g (44 mM) of 1-(1-bromopropyl)-2-bromomethylbenzene and 6 g (65 mM) of aminoacetonitrile hydrochloride to yield the title compound as a pale red oil which crystallised on cooling.

$^1$H-nmr δ (CDCl$_3$)
7.4–7.1 (4H,m); 4.24 (1H,d), 4.2–4.0 (1H,m); 3.98 (1H,d); 3.72 (2H,s); 2.0–1.7 (2H,m); 0.85 (3H,t).

EXAMPLE X 7

4-Chloro-1-(1-hydroxyethyl)-2-hydroxymethylbenzene

This compound was prepared in an analogous manner to Example X$^1$ from 6.0 g (32.8 mM) of 4-chloro-2-formylacetophenone and lithium aluminium hydride to yield the title compound as a colourless oil.

$^1$H-nmr δ (CDCl$_3$)
7.4–71. (3H,m); 4.95 (1H,q); 4.68 (1H,d); 4.38 (1H,d); 3.8–3.5 (2H,broad s, exchanges with D$_2$O); 1.45 (3H,t).

EXAMPLE X 8

1-(1-Chloroethyl)-2-chloromethyl-4-chlorobenzene

This compound was prepared in an analogous manner to Example X2 from 6.0 g (32 mM) of 4-chloro-1-(1-hydroxyethyl)-2-hydroxymethylbenzene using thionyl chloride instead of phosphorous tribromide, to yield the title compound as an oil.

$^1$H-nmr δ (CDCl$_3$)
7.5–7.1 (3H,m); 5.50 (1H,q); 4.88 (1H,d); 4.56 (1H,d), 1.98 (3H,d).

EXAMPLE X 9

2H-(5-Chloro-1-methyl-1,3-dihydroisoindole)-2-acetonitrile

This compound was prepared in an analogous manner to Example X3 from 3.0 g (13.4 mM) of 1-(1-chloroethyl)-2-chloromethyl-4-chlorobenzene and 2.0 g (21 mmol) of aminoacetonitrile hydrochloride to yield the title compound as a crystalline solid.

$^1$H-nmr δ (CDCl$_3$)
7.3–7.2 (2H,m); 7.05 (1H,d); 4.18 (1H,d); 4.03 (2H,s); 3.87 (1H,d); 3.77 (1H,d); 1.40 (3H,d).

EXAMPLE X 10

2-(4-Chloro-2-formylphenyl)-4,4-dimethyl-4,5-dihydrooxazole

To a solution of 16 g (76 mM) of 2-(4-chlorophenyl)-4,4-dimethyl-4,5-dihydrooxazole in 60 ml of dry tetrahydrofuran at −78° C. under an inert atmosphere was added dropwise 75 ml of 1.4M sec-butyllithium in hexane. After 1 hour 9.7 ml of freshly distilled dimethylformamide in 20 ml of tetrahydrofuran was added and stirring was continued for 2 hours at room temperature. The mixture was poured into water (200 ml) and extracted with diethylether (2×100 ml), dried and evaporated to yield the crude product. Vacuum distillation, bp 140–1500° C./0.4 mm gave the title compound as a pale yellow oil.

$^1$H-nmr δ (CDCl$_3$)
10.78 (1H,s); 8.0–7.7 (2H,m); 7.6–7,4 (1H,m); 4.11 (2H,s); 1.35 (6H,s).

EXAMPLE X 11

2-[4-Chloro-2-(1-hydroxyethyl)phenyl]-4,4-dimethyl-4,5-dihydrooxazole

To a suspension of 0.84 g (35 mM) of magnesium metal in 10 ml of diethyl ether was added dropwise 2.18 ml (35 mmol) of iodomethane. Once all the magnesium had dissolved the solution was added to 6.3 g (23.5 mmol) of 2-(4-chloro-2-formylphenyl)-4,4-dimethyl-4,5-dihydrooxazole in 10 ml of diethyl ether at 5° C.

After stirring overnight at room temperature the mixture was poured into water (200 ml) and extracted with diethyl ether (2×100 ml). Drying and evaporation yielded the title compound as a pale yellow oil.

$^1$H-nmr δ (CDCl$_3$)
7.75 (1H,d); 7.5–7.2 (2H,m); 7.05 (1H exchanges with D$_2$O); 5.00 (1H, q); 4.10 (2H, S); 1.50 (3H, d); 1.34 (6H,s).

EXAMPLE X 12

5-Chloro-7-methylphthalide 6.3 g (25 mM) of 2-[4-chloro-2-(1-hydroxyethyl) phenyl]-4,4-dimethyl-4,5-dihydrooxazole in 25 ml of 6N hydrochloric acid was heated for 1.5 hours under reflux in an inert atmosphere. The mixture was cooled and extracted with ethyl acetate. After drying and evaporation of the organic extracts the title compound was obtained as a pale yellow solid.

$^1$H-nmr δ (CDCl$_3$)
7.84 (1H, d); 7.6–7.4 (2H,m); 5.42 (1H, q); 1.60 (3H,d).

EXAMPLE X 13

5-Chloro-1-(1-hydroxyethyl)-2-hydroxymethylbenzene

This compound was prepared in an analogous manner to Example X1 from 4.6 g (25 mM) 5-chloro-7-methylphthalide and lithium aluminium hydride to yield the title compound as an oil.

$^1$H-nmr δ (CDCl$_3$)
7.38 (1H,s); 7.3–7.0 (2H,m); 4.91 (1H,q); 4.62 (1H,d); 4.33 (1H,d); 4.0–3.7 (2H,broad s, exchanges with D$_2$O); 1.40 (3H,s).

EXAMPLE X 14

(1-Bromoethyl)-2-bromomethyl-5-chlorobenzene

This compound was prepared in an analogous manner to Example X2 from 4.0 g (21,4 mM) of 5-chloro-1-(1-hydroxyethyl)-2-hydroxymethylbenzene and phosphorous tribromide to yield the title compound as an oil.

$^1$H-nmr δ (CDCl$_3$)
7.58 (1H,s); 7.4–7.1 (2H,m); 5.50 (1H,q); 4.72 (1H,d); 4.39 1H,d); 2.10 (3H,d).

EXAMPLE X 15

2H-(6-Chloro-1-methyl-1,3-dihydroisoindole)-2-acetonitrile

This compound was prepared in an analogous manner to Example X3 from 5.0 g (16 mM) of 1-(1-bromoethyl)-2-bromomethyl-5-chlorobenzene and 2.0 g (21 mM) of aminoacetonitrile hydrochloride to yield the title compound as an oil.

$^1$H-nmr δ (CDCl$_3$)
7.3–7.1 (3H,m); 4.3–4.0 (3H, m); 3.91 (1H,d); 3.78 (1H,d); 1.40 (3H,d).

EXAMPLE X 16

6-Fluoro-3-methylphthalide 30 g (19.8 mM) of 6-amino-3-methylphthalide dissolved in 250 ml of 6N hydrochloric acid and 200 ml of acetone at 5° C. was treated portionwise with 13.7 g (19.8 mM) of sodium nitrite. After stirring for 1.5 hours 55 g (550 mM) of sodium tetrafluoroborate in 50 ml of water was added and the mixture left at 5° C. overnight. The acetone was carefully evaporated under reduced pressure and the resultant solid filtered and dried under vacuum.

The diazonium tetrafluoroborate obtained was added to 75 ml of, nitrogen purged, xylene and heated at 130° C. for 0.25 hours. Upon cooling the mixture was treated with saturated sodium bicarbonate solution until alkaline and extracted with diethyl ether (3×50 ml). After drying and evaporation the crude product was obtained as a dark brown oil. Chromatography over silica gel eluting with dichloromethane gave the title compound as a low melting solid.

$^1$H-nmr δ (CDCl$_3$)
7.7–7.3 (3H, m); 5.64 (1H,q); 1.72 (3H,d).

EXAMPLE X 17

4-Fluoro-1-(1-hydroxyethyl)-2-hydroxymethylbenzene

This compound was prepared in an analogous manner to Example X1 from 8.0 (48 mM) of 6-fluoro-3-methylphthalide and lithium aluminium hydride to yield the title compound as a yellow oil.

$^1$H-nmr δ (CDCl$_3$)

7.5–7.2 (1H,m); 7.1–6.9 (2H,m); 4.95 (1H,q); 4.65 (1H,d); 4.40 (1H,d); 3.9–3.6 (2H,broad s, exchanges with D$_2$O); 1.42 (3H,d).

EXAMPLE X 18

1-(1-Bromoethyl)-2-bromomethyl-4-fluorobenzene

This compound was prepared in an analogous manner to Example X2 from 7.5 g (544 mM) of 4-fluoro-1-(1-hydroxyethyl)-2-hydroxymethyl benzene and phosphorous tribromide to yield the title compound as an oil which slowly crystallised at room temperature.

$^1$H-nmr δ (CDCl$_3$)

7.8–7.4 (1H,m); 7.3–6.8 (2H,m); 5.56 (1H,q); 4.75 (1H,d); 4.40 (1H,d); 2.10 (3H,d).

EXAMPLE X 19

2H-(5-Fluoro-1-methyl-1,3-dihydroisoindole)-2-acetonitrile

This compound was prepared in an analogous manner to Example X3 from 9.3 g (31.4 mM) of 1-(1-bromoethyl)-2-bromomethyl-4-fluorobenzene and 3.0 g (32.4 mM) of aminoacetonitrile hydrochloride to yield the title compound as a pale yellow oil.

$^1$H-nmr δ (CDCl$_3$)

7.3–6.9 (3H,m); 4.3–3.8 (3H,m); 3.80 (2H,s); 1.35 (3H,d).

EXAMPLE X 20

α-(4-Chlorophenyl)-1,2-benzenedimethanol

A mixture of 55 g (0.3M) of 2-(4-chlorobenzoyl) benzoic acid, 5 ml of concentrated sulphuric acid and 500 ml of methanol was heated under reflux for 3 hours. The mixture was evaporated and the residue was taken up in dichloromethane washed with water then aqueous sodium bicarbonate. The dichloromethane was dried and evaporated. The residue was then reduced with lithium aluminium hydride in an analogous manner to that described in Example X1 to give the title compound.

$^1$H nmr δ (CDCl$_3$)

7.22 (8H, m), 5.72 (1H,s); 4.35 (4H, brs, 2H exchange with D$_2$O).

EXAMPLE X 21

α-(2-Bromomethylphenyl)-4-chlorophenylmethyl bromide

Excess hydrogen bromide was bubbled through a solution of 28 g (0.11M) of α-(4-chlorophenyl)-1,2-benzenedimethanol in 250 ml of dichloromethane. After stirring for 12 hours at room temperature the mixture was dried and evaporated to give the title compound.

$^1$H nmr δ (CDCl$_3$)

7.3 (8H,m); 6.72 (1H,S) and 4.56 (2H,q).

EXAMPLE X 22

2H-(1-(4-Chlorophenyl)-1,3-dihydroisoindole)-2-acetonitrile

The title compound was prepared from 37.3 g (0.1M) of α-(2-bromomethylphenyl)-4-chlorophenyl methyl bromide, 13.82 g (0.15M) of aminoacetonitrile hydrochloride and 42 ml (0.3M) of triethylamine by an analogous method to that described in Example X3.

$^1$H nmr δ (CDCl$_3$)

6.68–7.53 (8H, m ), 4.92 (1H, brs), 4.2 (2H, m), and 3.8 (2H, q).

EXAMPLE X 23

α-(3-Chlorophenyl)-1,2-benzenedimethanol

Excess hydrogen chloride gas was bubbled though a solution of 25 g (0.14M) of 2-(3-chlorobenzoyl)benzoic acid in 1 liter of methanol. The mixture was then stirred at room temperature for 12 hours. The mixture was evaporated and the residue was taken up in dichloromethane washed with water then aqueous sodium bicarbonate. The dichloromethane was dried and evaporated. The residue was then reduced with lithium aluminium hydride in an analogous manner to that described in Example X1 to give the title compound.

$^1$H nmr δ (CDCl$_3$)

7.18 (8H, m); 5.75 (1H, s); 4.35 (4H, brs, 2H exchanges with D$_2$O).

EXAMPLE X 24

α-(2-Bromomethylphenyl)-3-chlorophenylmethyl bromide

Excess hydrogen bromide was bubbled through a solution of 21 g (84 mM) of α-(3-chlorophenyl)-1,2-benzenedimethanol in 250 ml of dichloromethane. After stirring for 12 hours at room temperature the mixture was dried and evaporated to give the title compound.

$^1$H nmr δ (CDCl$_3$)

7.4 (8H, m); 6.65 (1H, s) and 4.53 (2H, q).

EXAMPLE X 25

2H-(1-(3-Chlorophenyl)-1,3-dihydroisoindole)-2-acetonitrile

The title compound was prepared from 28 g (74.8 mM) of α-(2-bromomethylphenyl)-3-chlorophenylmethyl bromide, 11.5 g (0.12m) of aminoacetonitrile hydrochloride and 34.5 ml (0.25M) of triethylamine by an analogous method to that described in Example X3.

$^1$H nmr δ (CDCl$_3$)

6.68–7.63 (8H,m); 4.85 (1H, brs); 4.25 (2H, m) and 3.62 (2H, brs).

EXAMPLE X 26

α-(4-Fluorophenyl)-1,2-benzenedimethanol

Excess hydrogen chloride gas was bubbled through a solution of 50 g of 2-(4-fluorobenzoyl) benzoic acid in 1 liter of methanol. The mixture was then stirred at room temperature for 12 hours. The mixture was evaporated and the residue was taken up in dichloromethane washed with water then aqueous sodium bicarbonate. The dichloromethane was dried and evaporated. The residue in 1 liter of ether was reduced with 5.6 g of lithium borohydride under nitrogen gas. The ether was evaporated and the residue was partitioned between water and dichloromethane. The dichloromethane was dried and evaporated to give the title compound.

¹H nmr δ (CDCl₃)
6.7–7.32 (8H, m); 5.82 (1H, brs) and 4.3 (2H, brs).

EXAMPLE X 27

α-(2-Bromomethylphenyl)-4-fluorophenylmethyl bromide

The title compound was prepared from 40 g (0.17M) of α-(4-fluorophenyl)-1,2-benzenedimethanol and 40 ml (0.42M) of phosphorous tribromide in 200 ml of ether by an analogous procedure to that described in Example X2.

¹H nmr δ (CDCl₃)
6.78–7.7 (8H, m); 6.83 (1H, s) and 4.5 (2H, q).

EXAMPLE X 28

2H-(1-(4-Fluorophenyl)-1,3-dihydroisoindole)-2-acetonitrile

The title compound was prepared from 52.2 g (0.16M) of α-(2-bromomethylphenyl)-4-fluorophenyl methylbromide, 16.2 g (0.17M) of aminoacetonitrile hydrochloride and 62 ml (0.44M) of triethylamine by an analogous method to that described in Example X3.

¹H nmr δ (CDCl₃)
6.7–7.55 (8H, m); 4.9 (1H, brs); 4.2 (2H,m) and 3.62 (2H.brs).

EXAMPLE X 29

2H-(1-Phenyl-1,3-dihydroisoindole)-2-acetonitrile

The title compound, m.p. 106–107° C. (isopropanol), was prepared from 17.4 g (51 mM) of α-(2-bromomethylphenyl) phenylmethyl bromide, 7.1 g, (76 mM) of aminoacetonitrile hydrochloride and 21.5 ml (154 mM) of triethylamine by an analogous method to that described in Example X 4.

¹H nmr δ (CDCl₃)
7.4–6.6 (9H,m); 4.85 (1H, brs); 4.25 (2H, m) and 3.68 (2H, s).

EXAMPLE X30

1-(1-Methylethyl)phthalide

A mixture of 4 g (22.9 mM) of 1-(1-methylethenyl) phthalide and 50 mg of Adam's catalyst in 200 ml of ethanol was hydrogenated at atmospheric pressure. After the required amount of hydrogen was consumed the mixture was filtered and evaporated to yield the title compound as a pale yellow oil.

¹H - nmr δ (CDCl₃)
8.0–7.4 (4H, m); 5.40 (1H, d); 2.5–7.1 (1H, m); 1.10 (3H, d); 0.81 (3H, d).

EXAMPLE X31

1-Hydroxy methyl-2-(1-hydroxy-2-methylpropyl)benzene

This compound was prepared in an analogous manner to Example X1 from 3.9 g (22 mM) of 1-(1-methylethyl) phthalide and lithium aluminium hydride to yield the title compound as an oil.

¹H - nmr δ (CDCl₃)
7.5–7.0 (4H, m); 4.48 (2H, s); 4.33 (1H, d); 4.0–3.5 (2H, broad signal, exchanges with D₂O); 2.3–1.8 (1H, m); 1.05 (3H, d); 0.68 (3H, d).

EXAMPLE X32

1-Bromomethyl-2-(1-bromo-2-methylpropyl)benzene.

This compound was prepared in an analogous manner to Example X2 from 3.5 g (19.4 mmol) of 1-hydroxymethyl-2-(1-hydroxy-2-methylpropyl)benzene and phosphorus tribromide to yield the title compound as an oil.

¹H - nmr δ (CDCl₃)
7.6–7.1 (4H, m); 5.05 (1H, d); 4.65 (1H, d); 4.40 (1H, d); 2.8–2.3 (1H, m); 1.28 (3H, d); 0.86 (3H, d).

EXAMPLE X33

2H-[1-(1-Methylethyl)-1,3-dihydroisoindole]-2-acetonitrile hydrochloride

This compound was prepared in an analogous manner to Example X3 from 4.8 g (15.7 mM) of 1-bromomethyl-2-(1-bromo-2-methylpropyl)benzene and 1.5 g (16.2 mM) of aminoacetonitrile hydrochloride to yield the crude compound as an oil. This was dissolved in ethyl acetate and converted to the hydrochloride with hydrogen chloride to yield the title compound.

¹H - nmr δ (DMSO)
11.0–10.5 (1H, broad singlet, exchanges with D₂O); 7.5–7.2 (4H, m); 4.81 (1H, d); 5.50 (1H, d); 4.44 (1H, d); 3.34 (2H. s); 2.5–2.3 (1H, m); 1.03 (3H. d); 0.94 (3H, d).

EXAMPLE X34

α-(4-Methylphenyl)-1,2-benzenedimethanol.

The title compound was prepared from 2-(4-methylbenzoyl)benzoic acid by an analogous procedure to that described in Example X26.

¹H - nmr δ (CDCl₃)
6.9–7.37 (8H, m); 5.9 (1H, brs); 4.3 (2H, m) and 2.3 (3H, s).

EXAMPLE X35

α-(2-Bromomethylphenyl)-4-methylphenylmethyl bromide.

The title compound was prepared from 52 g (0.23M) of α-(4-methylphenyl)-1,2-benzenedimethanol and 50 ml (0.53M) of phosphorus tribomide in 1 liter of diethyl ether by an analogous procedure to that described in Example X2.

¹H - nmr δ (CDCl₃)
6.88–7.8 (8H, m); 6.7 (1H, s); 4.5 (2H, q) and 2.27 (3H, s).

EXAMPLE X36

2H-(1-(4-Methylphenyl)-1,3-dihydroisoindole)-2-acetonitrile.

The title compound was prepared from 70 g (0.2M) of α-(2-bromomethylphenyl)-4-methylphenylmethyl bromide, 22 g (0.23M) of aminoacetonitrile hydrochloride and 83 ml (0.6M) of triethylamine by an analogous method to that described in Example X3.

¹H - nmr δ (CDCl₃)
6.7–7.6 (8H, m); 4.83 (1H, brs); 4.15 (2H, m) 3.6 (2H, m) and 2.18 (3H, s).

EXAMPLE X37

α-(4-Methoxyphenyl)-1,2-benzenedimethanol.

The title compound was prepared from 2-(4-methoxybenzoyl)benzoic acid by an analogous procedure to that described in Example X26.

¹H - nmr δ (CDCl₃)
6.7–7.3 (8H, m); 5.73 (1H, brs); 4.3 (2H, brs) and 3.63 (3H, s).

EXAMPLE X38

α-(2-Bromomethylphenyl)-4-methoxyphenylmethyl bromide.

The title compound was prepared from 50 g (0.2M) of α-(4-methoxyphenyl)-1,2-benzenedimethanol and 50 ml (0.53M) of phosphorus tribromide in 1 liter of diethyl ether by an analogous procedure to that described in Example X2.

$^1$H - nmr δ (CDCl$_3$)

6.85–7.9 (8H, m); 6.7 (1H, s); 4.4 (2H, q) and 3.7 (3H, s).

EXAMPLE X39

2H-(1-(4-Methoxyphenyl)-1,3-dihydroisoindole)-2-acetonitrile.

The title compound was prepared from 53 g (0.14M) of α-(2-bromomethylphenyl)-4-methoxyphenylmethyl bromide, 16 g (0.17M) of aminoacetonitrile hydrochloride and 60 ml (0.43M) of triethylamine by an analogous method to that described in Example X3.

$^1$H - nmr δ (CDCl$_3$)

6.5–7.5 (8H, m); 4.9 (1H, brs); 4.2 (2H, m) and 3.7 (5H, m+s).

EXAMPLE X40

1-(Bromomethyl)-2-(2-phenyl-1-bromoethyl)benzene.

The title compound was prepared from 12.5 g (55 mM) of (1-hydroxymethyl)-2-(2-phenyl-1-hydroxyethyl)benzene and 5.7 ml (60 mM) of phosphorous tribromide in chloroform (150 ml) by an analogous procedure to that described in Example X2.

$^1$H - nmr δ (CDCl$_3$)

7.9–6.85 (9H, m); 5.5 (1H, t); 4.35 (2H, q) and 3.5 (2H, d).

EXAMPLE X41

2H-(1-Benzyl-1,3-dihydroisoindole)-2-acetonitrile

The title compound, m.p. 78–79° C. (isopropanol), was prepared from 19.8 g (56 mM) of 1-(bromomethyl)-2-(2-phenyl-1-bromoethyl)benzene, 7.8 g (84 mM) of amino acetonitrile hydrochloride and 23.4 ml (16.8 mM) triethylamine by an analogous method to that described in Example X4.

$^1$H - nmr δ (CDCl$_3$)

7.4–7.1 (9H, m); 4.4 (1H, m); 4.3 (1H, dd); 4.05 (1H, dd); 3.5 (1H, d); 3.25 (2H, m); and 2.8 (1H, dd).

Demonstration of Effectiveness of Compounds (A) Reversal of Adrenaline-Exacerbated Glucose Intolerance in Mice CFLP female mice of about 25 g were fasted for 24 hours prior to receiving water (10 ml/kg) or compounds by oral gavage. Thirty minutes later, glucose (1 g/kg) and adrenaline (300 ug/kg) were injected subcutaneously. Blood samples for glucose analysis were taken serially from the tail of each mouse at 0, 30, 60 90 and 120 minutes after dosing glucose and the results are expressed below as the percentage reduction in the area under the blood glucose curve; the compound treated groups being compared to the water dosed control group. Six mice were used in each treatment group.

| Example No | Dose (μmol/kg) | % Reduction in area under Blood Glucose curve |
|---|---|---|
| 1 | 20 | 34 |
| 2 | 20 | 27 |
| 3 | 10 | 41 |
| 4 | 20 | 27 |
| 5 | 5 | 20 |
| 6 | 20 | 15 |
| 7 | 20 | 22 |
| 8 | 20 | 21 |
| 9 | 20 | 31 |
| 12 | 20 | 34 |
| 13 | 20 | 16 |

(B) α2-Adrenoceptor Binding

Human platelet membranes were incubated with [$^3$H] Rauwolscine (0.5–1.0 nM) for 30 minutes at 30° C. with varying concentrates of the drug (0.1–10,000 nM). The binding assay was stopped by filtering and rinsing on GF/B glass fibre filters.

| Example No | Binding Affinity Ki (nM) |
|---|---|
| 1 | 1.7 |
| 2 | 4.1 |
| 3 | 3.4 |
| 4 | 6.4 |
| 5 | 0.8 |
| 6 | 3.6 |
| 7 | 1.8 |
| 8 | 2.7 |
| 9 | 6.9 |
| 10 | 34.0 |
| 11 | 25.0 |
| 12 | 2.0 |
| 13 | 40.0 |

We claim:

1. A compound of formula (I):

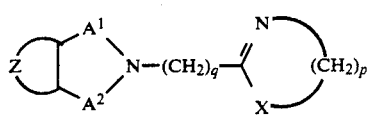

or a pharmaceutically acceptable salt, ester or amide thereof, or a pharmaceutically acceptable solvate thereof, wherein:

Z represents the optionally substituted benzene or naphthalene group;

one of A$^1$ and A$^2$ being an optionally substituted methylene group and the other being an optionally substituted ethylene group;

providing that at least one of A$^1$ and A$^2$ is substituted, substituents for A$^1$ and A$^2$ including up to four groups selected from an optionally substituted C$_{1-12}$-alkyl, an optionally substituted C$_{2-12}$-alkenyl, an optionally substituted C$_{2-12}$-alkynyl, an optionally substituted phenyl, naphthyl, phenyl-C$_{1-12}$-alkyl or naphthyl-C$_{1-12}$-alkyl;

X represents NR° wherein R° represents a hydrogen atom, an optionally substituted C$_{1-12}$-alkyl group, an optionally substituted phenyl or naphthyl group, a C$_{1-12}$-alkanoyl group an optionally substituted in the alkyl moiety, or a phenyl- or naphthyl- $C_{1-12}$-alkyl moiety an optionally substituted in the aryl moiety;

p represents an integer 2, and q represents an integer in the range of from 1 to 12;

and wherein the said include on the compound of formula (I) up to 5 groups selected from halogen, $C_{1-12}$-alkyl, $C_{2-12}$-alkenyl, $C_{2-12}$-alkynyl, phenyl, halo-$C_{1-12}$-alkyl, hydroxy, $C_{1-12}$-alkoxy, aryl-$C_{1-12}$-alkloxy, amino, mono- and di-$C_{1-12}$-alkylamino, amino-$C_{1-12}$alkyl, mono- and di-$C_{1-12}$-alkylamino-$C_{1-12}$-alkyl, nitro, carboxy, $C_{1-12}$-alkoxycarbonyl, carboxy-$C_{1-12}$-alkyl, $C_{1-12}$alkyoxycarbonyl-$C_{1-12}$-alkyl, $C_{1-12}$-alkylcarbonyl or a moiety $SO_2NR^sR^t$ wherein $R^s$ and $R^t$ each independently represent hydrogen or $C_{1-12}$-alkyl or $R^s$ and $R^t$ together with the nitrogen to which they are attached form a saturated 5- or 6-membered ring.

2. A compound, according to claim 1, wherein Z represents the residue of a substituted or unsubstituted phenyl group.

3. A compound, according to claim 1, wherein X represents $NR^o$.

4. A compound, according to claim 1, wherein X represents NH.

5. A compound, according to claim 1, wherein p represents the integer 2.

6. A compound, according to claim 1, wherein q represents the integer 1.

7. A pharmaceutical composition comprising a therapeutically effective amount of a compound of formula (I) as defined in claim 1, or a pharmaceutically acceptable salt, ester or amide thereof, or a pharmaceutically acceptable solvate thereof, and a pharmaceutically acceptable carrier therefor the composition being useful for the treatment or prophylaxis of hyperglycemia, glaucoma, hypertension, depression, or for inhibiting blood platelet aggegation.

8. A method for the treatment or prophylaxis of hyperglycaemia or hypertension in a human or non-human mammal which comprises administering an effective, non-toxic, amount of a compound of formula (I) as defined in claim 1, or a pharmaceutically acceptable salt, ester or amide thereof, or a pharmaceutically acceptable solvate thereof, to a human or non-human mammal in need thereof.

9. A method for the treatment or prophylaxis of glaucoma or the treatment of depression or inhibiting blood platelet aggregation in a human or non-human mammal, which method comprises administering an effective non-toxic amount of a compound of formula (I) as defined in claim 1, or a pharmaceutically acceptable salt, ester or amide thereof, or a pharmaceutically acceptable solvate thereof, to a human or non-human mammal in need thereof.

10. A compound according to claim 1 wherein Z is substituted with halogen.

11. A compound according to claim 1 wherein Z is substituted with fluorine or chlorine.

12. A compound according to claim 1 wherein $A^1$ and $A^2$ is substituted with $C_{1-12}$ alkyl, substituted or unsubstituted phenyl or benzyl.

13. A compound according to claim 1 wherein $A^1$ or $A^2$ is substituted with $C_{1-6}$ alkyl.

14. A compound according to claim 1 wherein $A^1$ or $A^2$ is substituted with methyl, ethyl or an iso-propyl group.

15. A compound according to claim 1, wherein $A^1$ or $A^2$ is substituted with phenyl or a phenyl group substituted with a halogen atom, a $C_{1-12}$ alkyl group or a $C_{1-12}$ alkoxy group.

16. A compound according to claim 1 wherein $A^1$ or $A^2$ is phenyl substituted with fluorine, chlorine, methyl or methoxy.

* * * * *

UNITED STATES PATENT AND TRADEMARK OFFICE
CERTIFICATE OF CORRECTION

PATENT NO.  : 5,077,299

DATED       : December 31, 1991

INVENTOR(S) : John M. Berge, et al.

It is certified that error appears in the above-identified patent and that said Letters Patent is hereby corrected as shown below:

In Claim 1, at column 25, line 5, after "and wherein the said"

add --optional substituents--.

Signed and Sealed this

Twenty-seventh Day of April, 1993

Attest:

MICHAEL K. KIRK

*Attesting Officer*  *Acting Commissioner of Patents and Trademarks*